United States Patent [19]
Luzzatto et al.

[11] Patent Number: 6,069,297
[45] Date of Patent: May 30, 2000

[54] GLUCOSE-6-PHOSPHATE DEHYDROGENASE DEFICIENT MICE AND METHODS OF USING SAME

[75] Inventors: Lucio Luzzatto; Letizia Longo, both of New York, N.Y.

[73] Assignee: Sloan-Kettering Institute for Cancer Research, New York, N.Y.

[21] Appl. No.: 08/985,758

[22] Filed: Dec. 5, 1997

Related U.S. Application Data

[60] Provisional application No. 60/037,337, Dec. 9, 1996.

[51] Int. Cl.[7] .......................... A01K 67/00; C12N 15/85; C12N 15/63; G01N 33/00
[52] U.S. Cl. .................................. 800/18; 800/8; 800/13; 800/14; 800/3; 435/320.1; 435/375; 435/354; 435/355; 435/455
[58] Field of Search .................................. 800/2, DIG. 1, 800/DIG. 3, 18, 3, 8, 9, 13, 14; 424/9.2; 435/325, 320.1, 354, 355, 455

[56] References Cited

PUBLICATIONS

Luzzatto, L. About hemoglobins, G6PD and parasites in red cells. Experientia 51. 206–208, 1995.

Pandolfi, P. et al. Targeted disruption of the housekeeping gene encoding glucose 6–phosphate dehydrogenase (G6PD). EMBO Journal. (14) 1995. p 5209–5215.

Martini, G. et al. A new lease of life for an old enzyme. Bioessays, Aug. 1996. (18) p 631–7.

Capecchi, M. Targeted gene replacement. Scientific American. Mar. 1994 (270) pp. 34–41.

Bradley, A. et al. Modifying the mouse: design and desire. Biotechnology 1992 (10) pp. 534–539.

*Primary Examiner*—John I. LeGuyader
*Assistant Examiner*—Michael C. Wilson
*Attorney, Agent, or Firm*—Oppedahl & Larson LLP

[57] ABSTRACT

Mice which produce measurable levels of glucose-6-phosphate dehydrogenase (G6PD) deficient red blood cells can be used as animal models to evaluate new drugs for risk of inducing hemolytic anemia in G6PD-deficient individuals, and for pre-clinical evaluation of gene therapy protocols to correct G6PD deficiency. Deficient and wild-type cells can be distinguished using a tetrazolium dye, and the numbers of each type of cell counted before and after exposure of the cells to the drug or therapy.

10 Claims, 1 Drawing Sheet

GLUCOSE-6-PHOSPHATE DEHYDROGENASE DEFICIENT MICE AND METHODS OF USING SAME

This application is filed under 35 USC § 111(a) claiming priority from US Provisional Application Serial No. 60/037,337 filed Dec. 9, 1996.

This application relates to mice which are defective in the gene encoding for the enzyme glucose-6-phosphate dehydrogenase (G6PD), and to the use of such mice in evaluation of hemolytic drugs and in pre-clinical gene therapy protocols.

G6PD is the first, and rate limiting enzyme of the pentose phosphate shunt in all cells, and it is therefore regarded as important in the biosynthesis of the sugar moiety of nucleic acids. In addition, in mammalian cells G6PD provides reductive potential in the form of NADPH.

Mutations in the gene encoding for G6PD that lead to deficient enzyme production have been associated with pathology in humans and animals, and specifically with instances of hemolytic anemia. In many cases, the deficiency is mild, and only manifests itself when drugs or other exogenous agents trigger hemolysis. In other cases, the deficiency is more severe, leading to chronic severe anemia and to a reduction in the ability of white blood cells to kill bacteria.

In order to evaluate new drugs for risk of inducing hemolytic anemia in G6PD-deficient individuals, and for pre-clinical evaluation of gene therapy protocols to correct G6PD deficiency, it would be advantageous to have an animal model which was defective in G6PD.

SUMMARY OF THE INVENTION

We have now succeeded in developing heterozygous mice which produce measurable levels of G6PD deficient red blood cells. These mice can be used as animal models to evaluate new drugs for risk of inducing hemolytic anemia in G6PD-deficient individuals, and for pre-clinical evaluation of gene therapy protocols to correct G6PD deficiency, it would be advantageous to have an animal model which was defective in G6PD. In addition, these mice and isolated G6PD-defective cells can be used for the production of additional mice with the same genotype, and potentially for the development of hemizygous mice which are completely deficient in G6PD production.

DETAILED DESCRIPTION OF THE INVENTION

Figure 1:
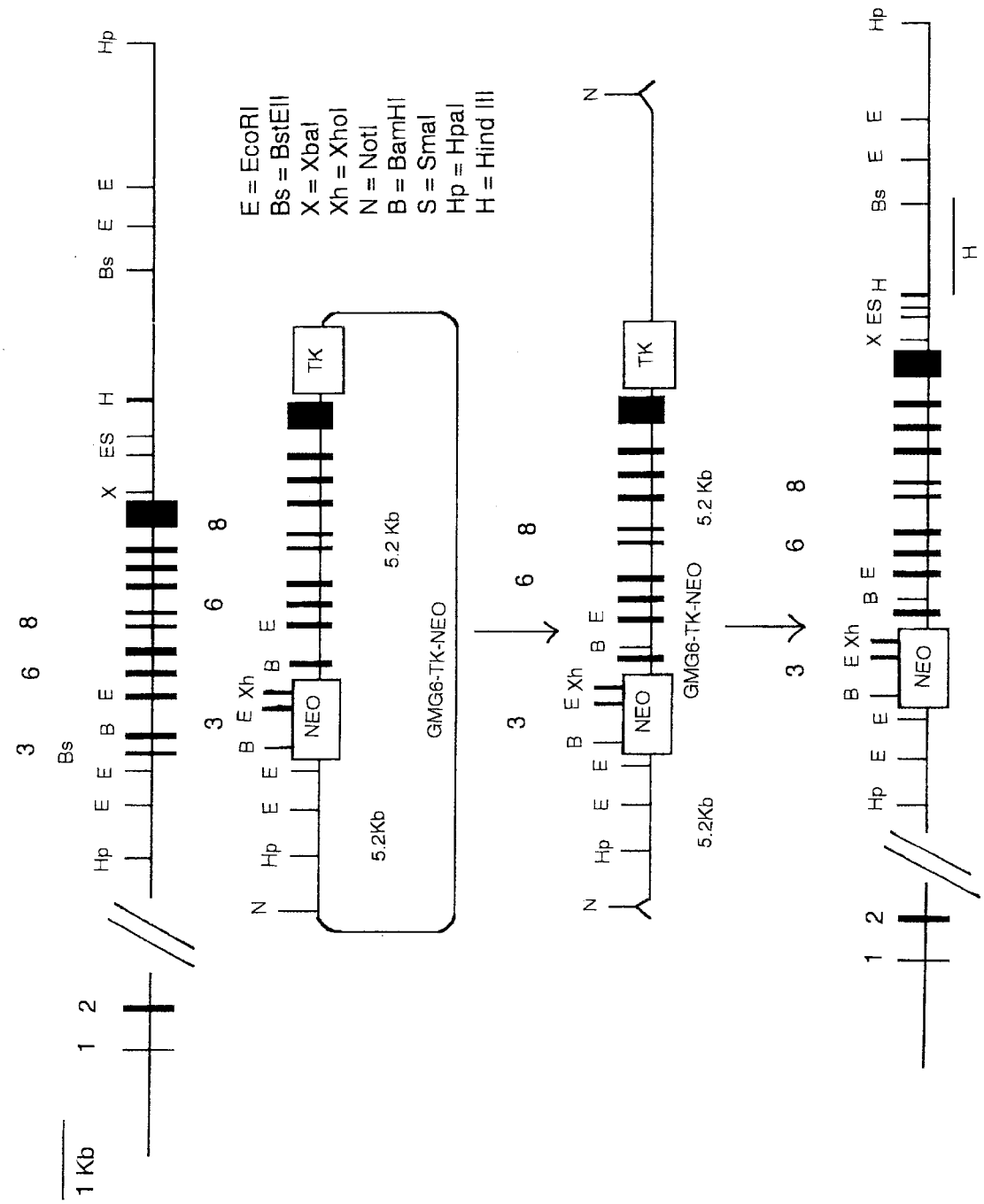
FIG. 1 shows insertion of a targeting vector to disrupt the murine G6PD gene.

In order to produce mice which are deficient in the production of functional G6PD, the first step is the disruption of the G6PD gene. The sequence for the coding region of the murine G6PD gene is known. (EMBL Accession No. Z11911, Zollo et al. *DNA Seq*. 3: 319–322 (1993). Disruption can be introduced into the gene by a variety of techniques based on targeted homologous recombination. In a preferred embodiment of the invention, the disruption is created in exon 3 of the murine G6PD gene using targeted homologous recombination in murine embryonic stem cells. Such recombinant embryonic stem cells which have this disrupted gene have been previously shown to be viable, although they are extremely sensitive to oxidative stress. See, Pandolfi et al., *EMBO J*. 14: 5209–5215 (1995). Disruption could also be carried out within exon 10, because it encodes residues important in dimerization of the G6PD subunit to active enzyme.

Embryonic stem cell clones shown by Southern blotting, by histochemical staining for G6PD activity and by spectrophotometric assay to be recombinant at the G6PD locus are injected into mouse blastocysts which are then surgically placed into the uterus of pseudo-pregnant foster mothers to generate chimeric mice. Coat color can be used as an indication of chimerism. Both male and female chimeric mice are obtained. Further breeding of male chimeric mice that are germ line transmitters of the G6PD defect with wild type female mice leads to the birth of offspring including heterozygous females. Breeding of these heterozygous females with wild type males produces offspring which may include hemizygous male G6PD-deficient mice, provided the deficiency in G6PD is not embryo-lethal.

G6PD-deficient mice in accordance with the invention can be used for evaluating the hemolytic potential of compositions, such as drugs. Red blood cells of heterozygous mice exhibit mosaicism in the expression of G6PD. Cells producing functional G6PD can be distinguished from G6PD-defective cells by cytochemical staining with tetrazolium dye. By quantifying the number of G6PD-defective cells present before and after administration of a compound being analyzed, the extent to which the compound induces hemolysis can be determined. Further, because the G6PD-defective cells make up a relatively small percentage of the total red blood cells in the heterozygous mouse, the test procedure is non-lethal to the mouse, and the same animal can be used for further tests after a period of time sufficient to build back up the level of G6PD-defective cells.

G6PD-deficient mice in accordance with this invention can also be used in preclinical evaluation of therapies, including gene therapies applicable to treatment of G6PD deficiency. For example, retroviral vectors or other gene transfer agents intended to restore G6PD function in a G6PD-deficient individual can be first tested in a G6PD-defective mouse using an assay similar to that used for evaluating hemolytic potential in a drug. By monitoring the number of D6PD-deficient cells before and after gene therapy an indication of the efficicacy of the therapy can be obtained.

Isolated cells which are G6PD-defective may also be used in the production of the new organisms by somatic cell cloning techniques. Similarly, such cells may themselves be used as targets for gene therapy or in the evaluation of hemolytic drugs.

The invention will now be further described by way of the following, non-limiting examples.

EXAMPLE 1

Construction of the Targeting Vector

Mouse G6PD clones were isolated from a genomic library from strain 129 ev in λ phage. The targeting vector GMG6-TK-NEO was constructed by insertion of the pMClNeo polyA+cassette (Stratagene, La Jolla, Calif.) into exon 3 of the murine G6PD gene. For this purpose, a BstEII site in exon 3 was blunted an transformed into an XhoI site utilizing commercial linkers. The NEO cassette, esxcised with a double XhoI/SalI digestion, was then cloned into the modified site in a transcriptional orientation opposite to that of the G6PD gene. The resulting construct was subsequently cloned next to the Herpes Virus Thymidine Kinase gene under the control of a mutated Polyoma enhancer (PY-TK;

see FIG. 1). The resulting targeting vector has approximately 10 kb of homology to the mouse genomic G6PD (5.2 kb upstream and 5.2 kb downstream of the NEO insertion). The targeting vector was linearized by NotI deigestion and electroporated into mouse Embryonic Stem (ES) cells.

EXAMPLE 2

ES Culture and Transfection

CJ7 ES cells were cultured in DMEM with 15% FCS on a feeder layer of mouse primary embryonic fibroblasts (PEF). For transfection, $10^7$ cells were resuspended in PBS with or without 30 μg of linearized targeting vector and subjected to a single shock (240 Volts at 500 μF). The selection was started 24 hours later in a medium containing 350 μg/ml G418 and 2 mM gancyclovir. After 8 days selection, 150 individual clones out of more than 200 double resistant clones were picked and grown individually.

EXAMPLE 3

Analysis of Double-Resistant ES Cell Clones

Genomic DNA from 129 ev mouse, wildtype CJ7 ES cells and targeted ES cell clones was isolated, digested with HpaI and XhoI restriction enzymes and fracitonated by electrophoresis on 0.6% agarose gel. Genomic DNA was subsequently transferred by alkaline capillary blotting to positively charged nylon membranes and hybridized to an HindIII/NotI 3'-G6PD genomic DNA fragment extenral to the targeting vector (Probe H; see FIG. 1). A band of 18 kb is detected if the muringe G6PD is in the wild-type confinguration. Due to an XhoI site present in the NEO cassette, a smaller band of 15 kb is detected is the gene is targeted. 10 clones out of 150 (6/6%) showed a restriction fragment consistent with recombination.

EXAMPLE 4

Histochemical Staining and Quantitation of G6PD

Sub-confluent ES cells in 24 well plates were stained according to a modified version of the method described by Wajnthal et al., *Biochem. Genet.* 1: 61–64 (1967). This method takes advanatge of the fact that NADPH produced by the G6PD reaction, in the presence of the electron carrier phenazine methosuplate, reduces a soluble tetrazolium dye to insoluble formazan. The cells were washed twice with PBS, then dried for about 5 minutes at 42° C. and placed in staining solution (10 mM G6P, 0.2 mM NADP, 0.5 mM MgCl$_2$, 12 mM NaN$_3$, 0.5 mg/ml Nitro Blue Tetrazolium, 0.02 mg/ml phenazine methosulphate in PBS/H$_2$O 4:1) at 37° C. in the dark for 30 minutes. The wells were then rinsed in PBS, mounted in glycerol and observed immediately. G6PD activity on cell extractants was measured quantitatively by the spectrophotometric assay described by Horecker et al., *Methods in Enzymology* Vol. 1 (1955).

EXAMPLE 5

Karyotype Analysis of ES Cell Clones

The 10 recombined ES cell clones were karyotyped and 9 of them were euploid.

EXAMPLE 6

Injection into Mouse Blastocyst and Generation of Chimeric Mice

Cells from one euploid recombined clone (#302) were injected into C57/BL6 host blastocysts and their surgical introduction into the uterus of pseudo-pregnant foster mothers was performed as described (Bradley, A, in Roberston, E. J., eds., *Teratocarcinoma and Embryonic Stem Cells, A Practical Approach,* IRL Press, Oxford, England (1987).). After 19 days, when all the pregnant mice delivered, 27 pups were obtained. Identification of chimeras was done on the basis of coat color 5–6 days after birth. Out of the newborn mice, 9 males and 3 females were chimeric. The percentage of chimerism, based on the color of the coat, was estimated to range from 40% to 60%.

The nine chimeric males were bred to C57/BL6 wild-type females to generate heterozygotes. From four of these males, no agouti offspring were obtained. 2 of these chimeric males were sterile and the other 2 chmieric males, after 5 crosses in which only black mice were born, were determined not to be germline transmitters.

Breeding of the remaining 5 chimeric males resulted in 102 newborn mice, 35 of which were agouti females, 31 agouti males and 36 black males and females. Thus, these five mice were all germline transmitters, and all the agouti females born from them are obligate heterozygotes for G6PD deficiency. The presence of the recombined allele was confirmed in 18 of the agouti females by genotyping with Southern blotting (utilizing Probe H with the diagnostic HpaI/XhoI digestion) and also by PCR using a pair of primers amplifying the NEO cassette.

Heterozygous females were bred with C57/BL6 wild-type males in an effort to generate hemizygous G6PD-deficient males. To date, no hemizygous mouse has been identified, suggesting that the hemizygous mutation may be embyrolethal.

EXAMPLE 7

Cytochemical analysis on red blood cells from heterzygote agouti females was performed to quantify the expression of G6PD deficiency. Cells were stained with tetrazolium dye as discussed above, and the number of stained and non-stained cells determined. In wild-type mice, out of 1000 cells, from 0 to 7 non-stained cells were detected. In G6PD-null heterozygotes, 10 to 40 cells out of 1000 are non-stained. Thus, there is a strong somatic selection against G6PD-null cells. Nevertheless, the levels of G6PD-null cells is sufficient to permit the heterozygote mice to be used for the analysis of chemical compounds for hemolytic potential.

Heterozygote mice having a detectable initial level of G6PD-null cells (for example 4%) are injected with a chemical compound to be evaluated for hemolytic potential. After about 2 days, the level of G6PD-null cells is again determined. Reduction in the number of G6PD-null cells which are more susceptible to hemolysis is consistent with the hemolytic activity of the compound tested.

What is claimed is:

1. A transgenic mouse whose genome comprises an induced heterozygous disruption of the glucose-6'-phosphate dehydrogenase gene which results in the mouse having a first portion of red blood cells producing a functionally defective glucose-6'-phosphate dehydrogenase enzyme; wherein the mouse has a second portion of red blood cells producing a functional glucose-6'-phosphate dehydrogenase; and wherein said first portion of red blood cells exhibits a greater susceptibility to hemolytic agents when compared to said second portion of red blood cells.

2. The transgenic mouse of claim 1, wherein the induced disruption is in exon 3 of the glucose-6'-phosphate dehydrogenase gene.

3. A method of evaluating the hemolytic potential of a composition comprising combining the composition with red blood cells from a transgenic mouse whose genome comprises an induced heterozygous disruption of the glucose-6'-phosphate dehydrogenase gene which results in the mouse having a first portion of red blood cells producing a functionally defective glucose-6'-phosphate dehydrogenase enzyme; wherein the mouse has a second portion of red blood cells producing a functional glucose-6'-phosphate dehydrogenase; and wherein said first portion of red blood cells exhibits a greater susceptibility to hemolytic agents when compared to said second portion of red blood cells; and determining the extent of hemolysis of red blood cells in the presence of the composition, wherein the extent of hemolysis correlates with the hemolytic potential of the composition.

4. The method of claim 3, wherein the induced disruption is in exon 3 of the glucose-6'-phosphate dehydrogenase gene.

5. The method of claim 3, wherein the extent of hemolysis is determined by staining red blood cells with a tetrazolium dye to determine levels of red blood cells which express no functional glucose-6'-phosphate dehydrogenase as a result of an induced disruption in a glucose-6'-phosphate dehydrogenase gene before and after combining the composition with red blood cells.

6. The method of claim 5, wherein the induced disruption is in exon 3 of the glucose-6'-phosphate dehydrogenase gene.

7. The method of claim 3, wherein the step of combining the composition with red blood cells is achieved by administering the composition to the transgenic mouse.

8. The method of claim 7, wherein the induced disruption is in exon 3 of the glucose-6'-phosphate dehydrogenase gene.

9. The method of claim 7, wherein the extent of hemolysis is determined by staining red blood cells with a tetrazolium dye to determine levels of red blood cells which express no functional glucose-6'-phosphate dehydrogenase as a result of an induced disruption in a glucose-6'-phosphate dehydrogenase gene before and after administration of the composition to the transgenic mouse.

10. The method of claim 9, wherein the induced disruption is in exon 3 of the glucose-6'-phosphate dehydrogenase gene.

* * * * *